United States Patent [19]

Benoit et al.

[11] Patent Number: 5,405,865
[45] Date of Patent: Apr. 11, 1995

[54] PYRETHROID ESTERS

[75] Inventors: Marc Benoit, Roquevaire; Jacques Demassey, Montevrain; Jean-Pierre Demoute, Neuilly Plaisance, all of France

[73] Assignee: Roussel-Uclaf, France

[21] Appl. No.: 12,723

[22] Filed: Feb. 3, 1993

[30] Foreign Application Priority Data

Feb. 7, 1992 [FR] France .................. 92 01391

[51] Int. Cl.⁶ ............. A01N 43/08; A01N 43/10
[52] U.S. Cl. .................. 514/438; 514/461; 514/471; 549/76; 549/79; 549/499
[58] Field of Search ............ 549/499, 76, 79; 514/438, 461, 471

[56] References Cited

FOREIGN PATENT DOCUMENTS

| | | |
|---|---|---|
| 1541893 | 10/1968 | France . |
| 2016577 | 5/1970 | France . |
| 2442826 | 2/1979 | France . |
| 2439780 | 10/1979 | France . |
| 0105006 | 4/1984 | France . |
| 2166237 | 7/1973 | Germany . |
| 0009709 | 4/1980 | Germany . |
| 1219830 | 1/1971 | United Kingdom . |

Primary Examiner—C. Warren Ivy
Assistant Examiner—A. A. Owens
Attorney, Agent, or Firm—Bierman & Muserlian

[57] ABSTRACT

A compound in all possible stereoisomeric forms and mixtures thereof of the formula

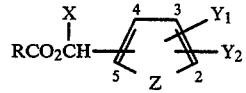

wherein the substituents are defined as in the specification having pesticidal properties.

16 Claims, No Drawings

PYRETHROID ESTERS

OBJECTS OF THE INVENTION

It is an object of the invention to provide the novel compounds of formula I and a novel process and intermediates for their preparation.

It is another object of the invention to provide novel pesticidal compositions and a novel method of combatting pests, especially insects.

These and other objects and advantages of the invention will become obvious in view of the following detailed description.

THE INVENTION

The novel compounds of the invention are a compound in all possible stereoisomeric forms and mixtures thereof of the formula

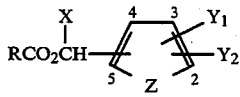  I wherein

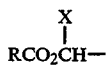

is in position 2 or 3, X is selected from the group consisting of hydrogen, alkyl of 1 to 8 carbon atoms and —C≡N, $Y_1$ and $Y_2$ are individually in position 2, 3, 4 or 5 and are selected from the group consisting of hydrogen, halogen

—$NO_2$, —$NH_2$, —CN, alkyl and alkoxy of 1 to 8 carbon atoms,

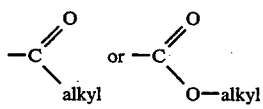

of up to 8 carbon atoms optionally substituted by at least one halogen atom and optionally unsaturated, —($CH_2$)$_n$OH, n is an integer of 0, 1, 2, 3 or 4 which OH can be optionally etherified or esterified and

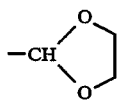

Z is oxygen or sulfur and R is:

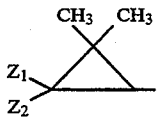

$Z_1$ and $Z_2$ are methyl, or $Z_1$ is hydrogen and either $Z_2$ is:

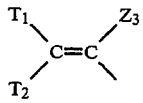

in which $Z_3$ is hydrogen or halogen and $T_1$ and $T_2$ are individually selected from the group consisting of hydrogen, halogen, alkoxy and alkyl of 1 to 8 carbon atoms optionally substituted by at least one member of the group consisting of halogen, mono-, di- or trifluoromethyl, cyano and phenyl optionally substituted by halogen, or $T_1$ and $T_2$ together form a cycloalkyl of 3 to 6 carbon atoms or:

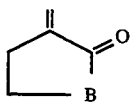

in which B is oxygen or sulfur; - or $Z_2$ is:

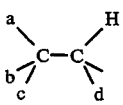

in which a, b, c and d are individually halogen- or $Z_2$ is:

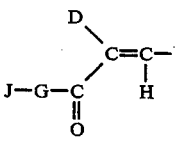

in which D is hydrogen or halogen or alkoxy of 1 to 8 carbon atoms, G is oxygen or sulfur and J is optionally unsaturated alkyl of up to 8 carbon atoms optionally substituted by at least one optionally different functional group, or aryl of 6 to 14 carbon atoms optionally substituted by at least one optionally different functional group, a heterocyclic optionally substituted by at least one optionally different functional group, or R is:

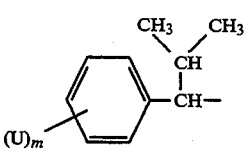

in which U, in any position on the benzene ring, is selected from the group consisting of halogen, alkyl of 1 to 8 carbon atoms and alkoxy of 1 to 8 carbon atoms, m is 0, 1 or 2 and when m is 2, the Us can be identical or different.

When $Y_1$ or $Y_2$ is halogen, it is preferably fluorine, chlorine or bromine. When X is a saturated or unsaturated alkyl, it is preferably methyl, ethyl or ethynyl. When $Y_1$ or $Y_2$ is alkyl, it is preferably methyl, ethyl, propyl, isopropyl, n-butyl, isobutyl, tert-butyl, vinyl, allyl, ethynyl or propynyl.

When $Y_1$ or $Y_2$ is substituted by halogen, the halogen is preferably fluorine or chlorine such as —$CF_3$, —$CHF_2$, —$CHCl_2$ or —$CH_2F$ or

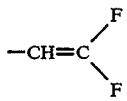

When $Y_1$ or $Y_2$ is O-alkyl, alkyl preferably has one of the values shown above. When Y is a free, etherified or esterified $(CH_2)_nOH$, it is preferably —$CH_2OH$, —$CH_2OCH_3$ or —$CH_2OCOCH_3$.

When $T_1$, $T_2$ or $Z_3$ is halogen, it is preferably fluorine, chlorine or bromine. When $T_1$ or $T_2$ is alkyl or alkoxy, it is preferably methyl, ethyl, propyl, methoxy, ethoxy or propoxy. a, b, c and d preferably are chlorine or bromine. When D is halogen, it is preferably fluorine, chlorine or bromine.

When J is alkyl substituted by at least one functional group, alkyl preferably has 1 to 8 carbon atoms such as methyl, ethyl, propyl, isopropyl, butyl, isobutyl or tert-butyl, and the functional group means one of those mentioned in European Application No. 50,534. J can also be alkyl substituted by aryl, especially an optionally substituted phenyl.

When J is alkyl substituted by one or more functional groups, there may be mentioned as preferred groups:
- —$(CH_2)_{n1}$—$C(Hal)_3$ in which $n_1$ is an integer from 1 to 8 and Hal is halogen such as $CH_2$—$CCl_3$, —$CH_2$—$CF_3$, —$CH_2$—$CH_2$—$CCl_3$ or $CH_2$—$CH_2$—$CF_3$;
- —$(CH_2)_{n2}$—$CH(Hal)_2$ in which Hal is defined as above and $n_2$ is a number from 0 to 8 such as —$CH_2$—$CHCl_2$, 13 $CH_2$—$CHF_2$ or —$CHF_2$;
- —$(CH_2)_{n1}$—$CH_2(Hal)$ in which $n_1$ and Hal are defined as above, for example —$CH_2$—$CH_2Cl$ or —$CH_2$—$CH_2F$;
- —$C(CHal_3)_3$ in which Hal is defined as above, for example —$C(CF_3)_3$ or —$C(CF_3)_2$—$CCl_3$, —$C(CF_3)_2$—$CH_3$, —$C(CH_3)_2$—$CF_3$, or —$C(CH_3)(CF_3)$—$CH_2$—$CH_3$, —$CH(CF_3)$—$CH_3$ or —$CH(CF_3)_2$, —$C(CH_3)_2$—$CN$, —$CH(CH_3)$—$CN$ or —$(CH_2)_n$—$CN$ in which n is defined as above, or —$CH(CN)$—$C(Hal)_3$ in which Hal is defined as above, for example —$CH(CN)$—$CCl_3$;
- —$(CH_2)_{n1}$—$OR_a$, in which $n_1$ is defined as above and $R_a$ is hydrogen or alkyl of 1 to 8 carbon atoms, for example —$CH_2$—$OCH_3$, —$CH_2$—$CH_2$—O—$CH_3$, —$CH_2$—$CH_2$—O—$CH_2$—$CH_3$ or —$CH_2$—$CH_2$—$OH$;

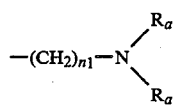

in which $n_1$ and $R_a$ are defined as above and the two $R_a$ can be different such as
—$CH_2$—$CH_2$—NH—$CH_3$, —$CH_2$—$CH_2$—$N(CH_3)_2$ or —$CH_2$—$CH_2$—$N(CH_3)$—$CH_2$—$CH_3$;

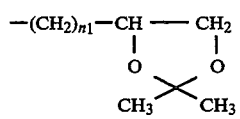

in which $n_1$ is defined as above, for example

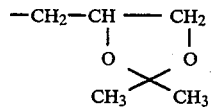

—$(CH_2)_{n1}$—$CH(OH)$—$CH_2$—$OH$ in which $n_1$ is defined as above, for example —$CH_2$—$CH(OH)$—$CH_2$—$OH$;

—$(CH_2)_{n1}$—O—THP in which $n_1$ is defined as above, and THP is 2-tetrahydropyranyl, for example —$CH_2$—O—THP or —$CH_2$—$CH_2$—O—THP;

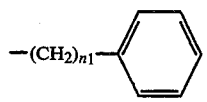

in which $n_1$ is defined as above, for example benzyl or phenethyl;

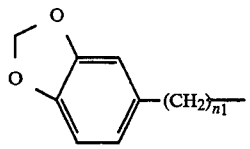

in which $n_1$ is defined as above, for example

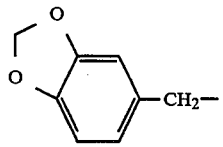

When J is an optionally substituted aryl, it is preferably an optionally substituted phenyl.

When J is a heterocyclic, it is preferably pyridyl, furyl, thienyl, oxazolyl or thiazolyl.

Among the preferred compounds of formula I are those wherein Z is oxygen, those wherein one of $Y_1$ and $Y_2$ is hydrogen, those wherein one of $Y_1$ and $Y_2$ is other than hydrogen in the 4- or 5- position and

is in the 2- position, those wherein $Y_1$ or $Y_2$ is alkyl of 1 to 4 carbon atoms optionally substituted by at least one fluorine, more preferably —$CHF_2$ or —$CF_3$, those wherein $Y_1$ or $Y_2$ is —$NO_2$, —C≡CH or —$CH_2$—C≡CH and those wherein X is hydrogen or ethynyl.

Preferably, R in the compounds of formula I is the residue of an acid derived from cyclopropane carboxylic acid wherein the cyclopropane copula has 1R, cis structure and more preferably

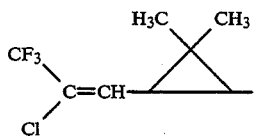

in all possible stereoisomeric forms, as well as their mixtures. The preferred compounds are those of Examples 1, 5, 7, 9, 10, 12, 18, 19, 26, 27, 28, 30 and 37 and most preferably Example 2.

The novel process of the invention for the preparation of a compound of formula I comprises reacting a compound of the formula

RCOOH      II wherein R has the above definition with an alcohol of the formula

in which X, Y and Z are defined as above, or a functional derivative thereof, to obtain the corresponding compound of formula I.

The functional acid derivative used is preferably an acid chloride. When the acid of formula II is reacted with the alcohol of formula III, the reaction is preferably carried out in the presence of dicyclohexylcarbodiimide.

The acids of formula II used are known products used in the synthesis of pyrethrinoid compounds.

The alcohols of formula III are new products and are an object of the invention. They can be prepared by analogy with the products whose preparation is given below in Preparations 1 and 2, and which can be schematised as follows:

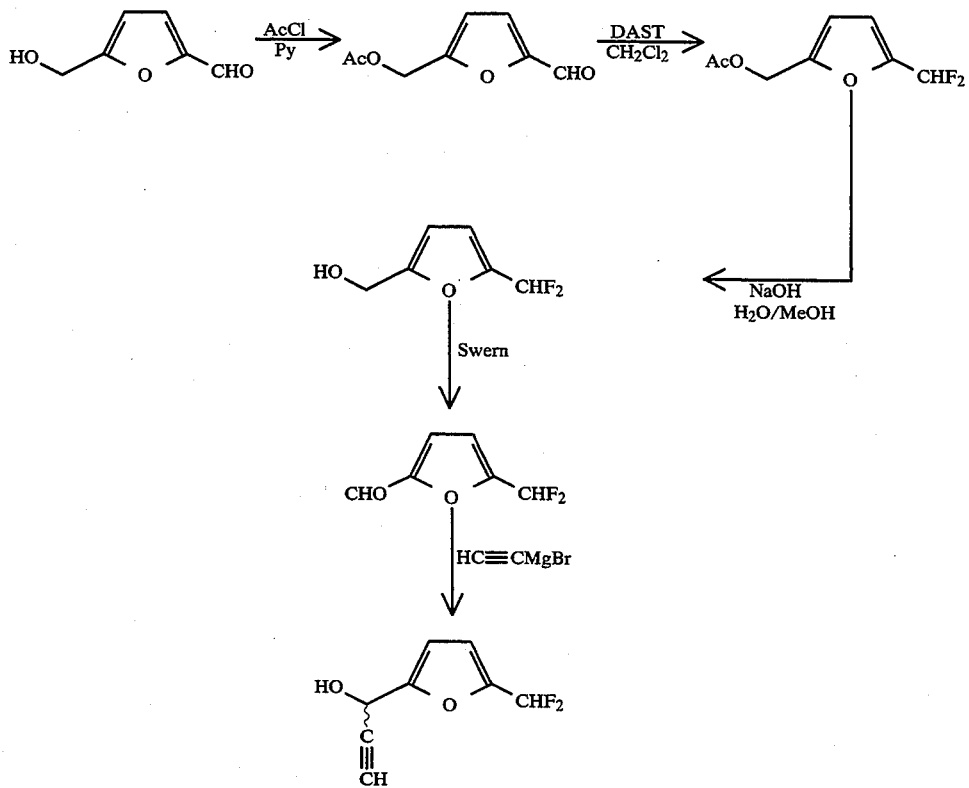

The compounds of formula III in which Z is sulfur can be prepared by analogy by the following process:

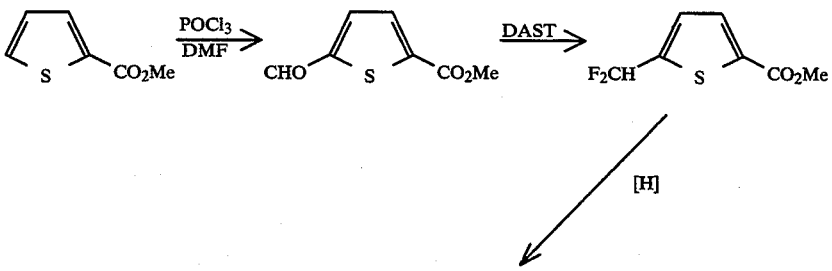

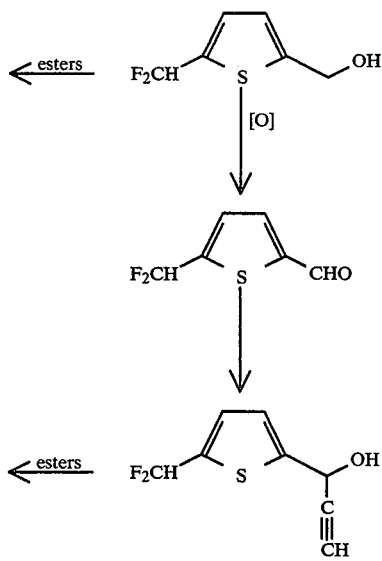

The compounds of formula I exhibit advantageous properties which make it possible to use them in controlling parasites. It may be, for example, the control of plant parasites, parasites which infest premises or parasites of warm-blooded animals. It is therefore possible to use the products of the invention for controlling insects, nematodes and members of the Acarida which are parasites of plants and animals, especially to control plant parasites, parasites which infest premises and parasites of warm-blooded animals.

The products of formula I can also be used for controlling insects and other soil parasites, for example Coleoptera such as Diabrotica, wireworms and white grubs, millipedes such as Scutigerellae and Blaniuli, and Diptera such as *Cecid midges*, and Lepidoptera such as the soil-dwelling Noctua species. They are used at doses of between 10 g and 300 g of active material to the hectare.

The products of formula I can also be used for controlling insects in premises, especially for controlling flies, mosquitoes and cockroaches.

The products of formula I are more stable to light and have little toxicity for mammals. This set of properties makes the products of formula I correspond perfectly to the demands of the modern agrochemical industry since they make it possible to protect crops while safeguarding the environment.

The products of formula I can also be used for controlling members of the Acarida and nematodes which are parasites of plants. The compounds of formula I can also be used for controlling members of the Acarida which are parasites of animals, for controlling, for example, ticks and especially ticks of the Boophilus species, those of the Hyalomnia species, those of the Amblyomnia species and those of the Rhipicephalus species or for controlling all kinds of itches and especially sarcoptic mange, psoroptic scabies and chorioptic mange.

The insecticidal compositions containing, as active principle, at least one of the products defined above are prepared according to the standard processes of the agrochemical industry or of the veterinary industry or of the industry of products intended for animal nutrition.

In those compositions intended for agricultural use and for use in premises, the active material(s) can optionally have one or more other pesticidal agents added. These compositions can be provided in the form of powders, granules, suspensions, emulsions, solutions, solutions for aerosols, combustible strips, baits or other preparations conventionally employed for the use of this type of compound.

Besides the active principle, these compositions generally contain a vehicle and/or a nonionic surface-active agent which additionally provides a uniform dispersion of the components of the mixture. The vehicle used can be a liquid, such as water, alcohol, hydrocarbons or other organic solvents, an inorganic, animal or vegetable oil, a powder such as talc, clays, silicates or kieselguhr, or a combustible solid.

The insecticidal compositions of the invention preferably contain from 0.005 % to 10 % by weight of active material. According to an advantageous procedure, for use in buildings, the compositions of the invention are used in the form of fumigant compositions which can advantageously consist of, for the nonactive part, a combustible insecticidal coil or also a noncombustible fibrous substrate. In the latter case, the fumigant obtained after incorporation of the active material is placed on a heating apparatus such as an electrical vaporiser.

In the case where an insecticidal coil is used, the inert support can be, for example, composed of pyrethrum marc, Tabu powder (or powder of *Machilus thumbergii* leaves), pyrethrum stalk powder, cedar leaf powder, wood starch powder (such as pine sawdust) and coconut shell powder. The dose of active material can be, for example, from 0.03 to 1% by weight. In the case where a noncombustible fibrous support is used, the dose of active material can be from 0.03 to 95% by weight.

The compositions of the invention for use in premises can also be obtained by preparing a sprayable oil based on the active principle, which oil impregnates the wick of a lamp and is then subjected to combustion. The concentration of the active principle incorporated in the oil is preferably from 0.03 to 95% by weight.

The acaricidal and nematocidal compositions contain, as active principle, at least one of the products of formula I defined above.

The insecticidal compositions of the invention, as well as the acaricidal and nematocidal compositions, can optionally have one or more other pesticidal agents added. The acaricidal and nematocidal compositions can especially be provided in the form of powders, granules, suspensions, emulsions or solutions.

For acaricidal use, wettable powders for foliar spraying containing from 1 to 80% by weight of active principle or liquids for foliar spraying containing from 1 to 500 g/l of active principle are preferably used. It is also possible to employ powders for foliar dusting containing from 0.05 to 3% of active material. For nematocidal use, liquids are preferably used for soil treatment containing from 300 to 500 g/l of active principle. The acaricidal and nematocidal compositions of the invention are preferably used at doses of between 1 and 100 g of active material to the hectare.

To increase the biological activity of the products of the invention, they can be added to conventional synergists such as 1-(2,5,8-trioxa-dodecyl)-2-propyl-4,5-(methylenedioxy)benzene (or piperonyl butoxide) or N-(2-ethylheptyl)bicyclo[2,2,1]hept-5-ene-2,3-dicarboximide, or piperonal bis[2-(2-butoxyethoxy)ethyl]acetal (or tropital).

The compounds of formula I exhibit an excellent general tolerance, and thus the products of formula I are especially useful for controlling ailments caused by ticks and itch mites in man and animals. The products are especially used for controlling lice as preventatives or curatives and for controlling itch mites.

The products of the invention can be administered externally, by spraying, by shampoo, by bath or painting and having a veterinary use which can also be administered by painting the backbone by the so-called "pour-on" method.

The compositions may also be used as biocides or as growth regulators.

The compositions possessing insecticidal, acaricidal or nematocidal activity may also contain as active material at least one of the compounds of formula I and at least one of the pyrethroid esters chosen from the group consisting of the allethrolone, (3,4,5,6-tetrahydrophthalimido)methyl alcohol, (5-benzyl-3-furyl)methyl alcohol, 3-phenoxybenzyl alcohol and alpha-cyano-3-phenoxybenzyl alcohol esters of chrysanthemic acids, of the (5-benzyl-3-furyl)methyl alcohol esters of 2,2-dimethyl-3-((2-oxo-3-tetrahydrothiophenylidene)methyl)cyclopropanecarboxylic acids, of the 3-phenoxybenzyl alcohol and alpha-cyano-3-phenoxybenzyl alcohol esters of 2,2-dimethyl-3-(2,2-dichlorovinyl)cyclopropanecarboxylic acids, of the alphacyano-3-phenoxybenzyl alcohol esters of 2,2-dimethyl-3-(2,2-dibromovinyl)cyclopropanecarboxylic acids, of the 3-phenoxybenzyl alcohol esters of 2-(para-chlorophenyl)-2-isopropylacetic acids, of the allethrolone, (3,4,5,6-tetrahydrophthalimido)methyl alcohol, (5-benzyl-3-furyl)methyl alcohol, 3-phenoxybenzyl alcohol and alpha-cyano-3-phenoxybenzyl alcohol esters of 2,2-dimethyl-3-(1,2,2,2-tetrahaloethyl)cyclopropanecarboxylic acids, in which "halo" represents a fluorine, chlorine or bromine atom, it being understood that the compounds (I) can exist in all their possible stereoisomeric forms as well as the acid and alcohol copulas of the above pyrethroid esters.

In the following examples, there are described several preferred embodiments to illustrate the invention. However, it should be understood that the invention is not intended to be limited to the specific embodiments.

EXAMPLE 1

(5-difluoromethyl-2-furyl)methyl [1R-[1α,3α,(Z)]]-2,2-dimethyl-3-(3,3,3-trifluoro-2-chloropropenyl)cyclopropanecarboxylate.

A mixture of 800 mg of 5-difluoromethyl-2-furanmethanol, 25 ml of methylene chloride and 1.4 g of [1R-[1α,3α(Z)]]-2,2-dimethyl-3-(3,3,3-trifluoro-2-chloropropenyl]cyclopropanecarboxylic acid was cooled to 5° C. and a solution of 1.2 g of DCC, 60 mg of DMAP and 15 ml of methylene chloride was added at 5° C. The reaction mixture stood at room temperature and was stirred for 2 hours. 10 ml of hexane were added, the mixture was stirred for 5 minutes, filtered and concentrated. The product was chromatographed on silica by eluting with a 95/5 cyclohexane/ethyl acetate mixture to obtain 2.01 g of a product which was filtered and dried to obtain 1.42 g of the desired product.

Preparation 1

5-difluoromethyl-2-furanmethanol.

Stage A: 5-acetyloxymethyl-2-furancarboxaldehyde.

10.05 ml of acetyl chloride were added at 5° C. to a solution of 16.2 g of 5-hydroxymethyl-2-furancarboxaldehyde and 200 ml of methylene chloride and 11.4 ml of pyridine and 50 ml of methylene chloride were then added. The reaction mixture was stirred for 3 hours at 20° C. and the reaction mixture was treated with an aqueous sodium dihydrogenphosphate solution and extracted with methylene chloride. The extract was dried and concentrated to obtain 19.35 g of the desired product after chromatography on silica by eluting with a hexane/ethyl acetate (7/3) mixture.

Stage B: Acetate of 5-difluoromethyl-2-furanmethanol.

A solution of 7.26 ml of DAST (diethylaminosulfur trifluoride) and 30 ml of methylene chloride was added at 5° C. to a solution of 10 g of the product of Stage A and 100 ml of methylene chloride. The mixture was stirred at 20° C. for half an hour and then refluxed for 1 hour. The mixture was stirred for 18 hours at 20° C. and then refluxed for 3 hours. The mixture was treated with sodium bicarbonate and extracted with methylene chloride. The extract was dried and concentrated to obtain 12 g of a product which was chromatographed on silica by eluting with an 8/2 hexane/ethyl acetate mixture to obtain 5.5 g of the desired product.

Stage C: 5-difluoromethyl-2-furanmethanol.

34.8 ml of a normal sodium hydroxide solution were added to a solution of 5.5 g of the product of Stage B and 100 ml of methanol. The mixture was stirred for 1 hour at 20° C. and then treated with a saturated sodium dihydrogenphosphate solution. The mixture was concentrated and the product was chromatographed on silica by eluting with a 7/3 hexane/ethyl acetate mixture to obtain 3.6 g of the desired product.

EXAMPLE 2

(5-difluoromethyl-2-furyl)-2-propynyl [1R-[1α,3α(Z)]]-2,2-dimethyl-3-(3,3,3-trifluoro-2-chloropropenyl)cyclopropanecarboxylate.

Using the procedure of Example 1, 1.69 g of [1R-[1α,3α(Z)]]-2,2-dimethyl-3-(3,3,3-trifluoro-2-chloropropenyl)cyclopropanecarboxylic acid and 1.2 g of (5-difluoromethyl-2-furyl)-2-propynol, were reacted to obtain 2.47 g of the desired product after chromatography.

Preparation 2

5-difluoromethyl-α-ethynyl-2-furanmethanol.

Stage A: 5-difluoromethyl-2-furancarboxaldehyde.

A solution of 6.5 ml of DMSO (dimethyl sulfoxide) and 60 ml of methylene chloride was added at −60° C. under a nitrogen atmosphere to a solution of 3.84 ml of oxalyl chloride and 40 ml of methylene chloride. The reaction mixture was stirred at −60° C. and 3.6 g of 5-difluoromethyl,2-furanmethanol in solution in 30 ml of methylene chloride were added. The mixture was stirred for 2 hours at −60° C. and a solution of 16.1 ml of triethylamine and 30 ml of methylene chloride was added over 15 minutes. The reaction mixture was stirred for half an hour at −60° C., the temperature was allowed to rise to −20° C. The mixture was stirred for half an hour at this temperature and then poured into a solution of sodium dihydrogenphosphate and extracted with methylene chloride. The extract was dried and the 3.6 g of product were chromatographed on silica by eluting with an 8/2 hexane/ethyl acetate mixture to obtain after chromatography, 2.5 g of the desired product.

Stage B: (5-difluoromethyl-2-furyl)-2-propynol.

43 ml of a 0.5M solution of ethynyl magnesium bromide in tetrahydrofuran were added at 0° C. over one hour to a solution of 2.5 g of the product of Stage A and 30 ml of tetrahydrofuran. The reaction mixture was stirred at 0° C. for 1 hour and then was poured into a saturated aqueous sodium dihydrogenphosphate solution. The 3 g of product were chromatographed on silica by eluting with a 7/3 hexane/ethyl acetate mixture to obtain 2.5 g of the desired product.

Using the procedure of Example 1 or 2 the appropriate alcohol and acid were reacted to obtain the following products:

EXAMPLE 3

(5-difluoromethyl-2-furyl)methyl [1R-[1α,3α(Z)]]-2,2-dimethyl-3-(2-fluoro-3-methoxy-3-oxo-1-propenyl)cyclopropanecarboxylate.

EXAMPLE 4

(5-difluoromethyl-2-furyl)methyl [1R-[1α,3α(Z)]]-2,2-dimethyl-3-(2,2-difluorocyclopropylidene)methyl cyclopropanecarboxylate.

EXAMPLE 5

1-(5-difluoromethyl-2-furyl)2-propynyl [1R-[1α,3α(Z)]]-2,2-dimethyl-3-(2-fluoro-3-methoxy-3-oxo-1-propenyl)cyclopropanecarboxylate.

EXAMPLE 6

1-(5-difluoromethyl-2-furyl)methyl [1R-[1α,3α(Z)]]-2,2-dimethyl-3-(2-fluoro-3-(tert-butoxy)-3-oxo-1-propenyl)cyclopropanecarboxylate.

EXAMPLE 7

1-(5-difluoromethyl-2-furyl)methyl [1R-[1α,3α(Z)]]-2,2-dimethyl-3-(2,2-dichloroethenyl)cyclopropanecarboxylate.

EXAMPLE 8

(5-difluoromethyl-2-furyl)methyl [1R-[1α,3α(Z)]]-2,2-dimethyl-3-[2-chloro-2-(4-chlorophenyl)ethenyl]cyclopropanecarboxylate.

EXAMPLE 9

1-(5-difluoromethyl-2-furyl)2-propynyl [1R-[1α,3α(Z)]]-2,2-dimethyl-3-(2,2-difluorocyclopropylidene)-methyl cyclopropanecarboxylate.

EXAMPLE 10

1-(5-difluoromethyl-2-furyl)-2-propynyl [1R-[1α,3α(Z)]]-2,2-dimethyl-3-[3-(1-trifluoromethyl)-(2,2,2-trifluoroethoxy)-3-oxo-1-propenyl]cyclopropanecarboxylate.

EXAMPLE 11

1-(5-dichloromethyl-2-furyl)-2-propynyl [1S-[1α,3α]]-2-isopropyl-2-(para-chlorophenyl)acetate.

EXAMPLE 12

(S)-1-(5-difluoromethyl-2-furyl)-2-propynyl [1R-[1α,3α(Z)]]-2,2-dimethyl-3-(3,3,3-trifluoro-2-chloropropenyl)cyclopropanecarboxylate and (R)-1-(5-difluoromethyl-2-furyl)-2-propynyl [(1R)-[1α,3α,(Z)]]-2,2-dimethyl-3-(3,3,3-trifluoro-2-chloropropenyl)cyclopropanecarboxylate.

EXAMPLE 13

1-(5-difluoromethyl-2-furyl)-2-propynyl [1R-[1α,3β(Z)]]-2,2-dimethyl-3-(2-fluoro-1-propenyl)cyclopropanecarboxylate. carboxylate.

EXAMPLE 14

1-(4-difluoromethyl-2-furyl)-2-propynyl [1R-[1α,3α(Z)]]-2,2-dimethyl-3-(3,3,3-trifluoro-2-chloropropenyl)cyclopropanecarboxylate.

EXAMPLE 15

(2-trifluoromethyl-3-furyl)methyl [1R-[1α,3α(Z)]]-2,2-dimethyl-3-(3,3,3-trifluoro-2-chloropropenyl)cyclopropanecarboxylate.

$R_f$=0.25 (hexane/isopropyl ether 95/5).

EXAMPLE 16

(2-trifluoromethyl-3-furyl)methyl [1R-[1α,3α(Z)]]-2,2-dimethyl-3-(2-fluoro-3-methoxy-3-oxo-1-propenyl)cyclopropanecarboxylate.

$R_f$=0.15 (hexane/AcOEt 9/1).

EXAMPLE 17

(2-trifluoromethyl-5-propynyl-3-furyl)methyl [1R-[1α,3α(Z)]]-2,2-dimethyl-3-(3,3,3-trifluoro-2-chloropropenyl)cyclopropanecarboxylate.

$R_f$=0.15 (hexane/AcOEt 95/5).

EXAMPLE 18

1-(5-trifluoromethyl-2-furyl)-2-propynyl [1R-[1α,3α(Z)]]-2,2-dimethyl-3-(3,3,3-trifluoro-2-chloropropenyl)cyclopropanecarboxylate.

$R_f$=0.2 (hexane/AcOEt 95/5).

EXAMPLE 19

1-(5-trifluoromethyl-2-furyl)-2-propynyl [1R-[1α,3α(Z)]]-2,2-dimethyl-3-(2-fluoro-3-methoxy-3-oxo-1-propenyl)cyclopropanecarboxylate.

$R_f$=0.15 (hexane/AcOEt 9/1).

EXAMPLE 20

1-(2-furyl)-2-propynyl [1R-[1α,3α(Z)]]-2,2-dimethyl-3-(3,3,3-trifluoro-2-chloropropenyl)cyclopropanecarboxylate.

$R_f$=0.25 (hexane/AcOEt 95/5).

EXAMPLE 21

1-(2-furyl)-2-propynyl [1R-[1α,3α(Z)]]-2,2-dimethyl-3-(2-fluoro-3-methoxy-3-oxo-1-propenyl)cyclopropanecarboxylate.
$R_f$=0.15 (hexane/AcOEt 9/1).

EXAMPLE 22

(5-methoxymethyl-2-furyl)methyl [1R-[1α,3α(Z)]]-2,2-dimethyl-3-(3,3,3-trifluoro-2-chloropropenyl)cyclopropanecarboxylate.
$R_f$=0.3 (hexane/AcOEt 8/2).

EXAMPLE 23

(5-methoxymethyl-2-furyl)methyl [1R-[1α,3α(Z)]]-2,2-dimethyl-3-(2-fluoro-3-methoxy-3-oxo-1-propenyl)cyclopropanecarboxylate.
$R_f$=0.17 (hexane/AcOEt 8/2).

EXAMPLE 24

1-(5-methoxymethyl-2-furyl)-2-propynyl [1R-1α,3α(Z)]]-2,2-dimethyl-3-(3,3,3-trifluoro-2-chloropropenyl)cyclopropanecarboxylate.
$R_f$=0.24 (hexane/AcOEt 8/2).

EXAMPLE 25

1-(5-methoxymethyl-2-furyl)-2-propynyl [1R-1α,3α(Z)]]-2,2-dimethyl-3-(2-fluoro-3-methoxy-3-oxo-1-propenyl)cyclopropanecarboxylate.
$R_f$=0.15 (hexane/AcOEt 8/2).

EXAMPLE 26

(5-ethynyl-2-furyl)methyl [1R-[1α,3α(Z)]]-2,2-dimethyl-3-(3,3,3-trifluoro-2-chloropropenyl)cyclopropanecarboxylate.
$R_f$=0.23 (hexane/AcOEt 95/5).

EXAMPLE 27

1-(5-ethynyl-2-furyl)-2-propynyl [1R-[1α,3α(Z)]]-2,2-dimethyl-3-(3,3,3-trifluoro-2-chloropropenyl)cyclopropanecarboxylate.
$R_f$=0.24 (hexane/AcOEt 8/2).

EXAMPLE 28

(2-difluoromethyl-4-furyl)methyl [1R-[1α,3α(Z)]]-2,2-dimethyl-3-(3,3,3-trifluoro-2-chloropropenyl)cyclopropanecarboxylate.
$R_f$=0.2 (hexane/AcOEt 95/5).

EXAMPLE 29

(2-difluoromethyl-4-furyl)methyl [1R-[1α,3α(Z)]]-2,2-dimethyl-3-(2-fluoro-3-methoxy-3-oxo-1-propenyl)cyclopropanecarboxylate.
$R_f$=0.25 (hexane/AcOEt 8/2).

EXAMPLE 30

1-(2-difluoromethyl-4-furyl)-2-propynyl [1R-[1α,3α(Z)]]-2,2-dimethyl-3-(3,3,3-trifluoro-2-chloropropenyl)cyclopropanecarboxylate.
$R_f$=0.15 (hexane/AcOEt 95/5).

EXAMPLE 31

1-(2-difluoromethyl-4-furyl)-2-propynyl [1R-[1α,3α(Z)]]-2,2-dimethyl-3-(2-fluoro-3-methoxy-3-oxo-1-propenyl)cyclopropanecarboxylate.
$R_f$=0.15 (hexane/isopropyl ether 8/2).

EXAMPLE 32

(2-difluoromethyl-3-furyl)methyl [1R-[1α,3α(Z)]]-2,2-dimethyl-3-(3,3,3-trifluoro-2-chloropropenyl)cyclopropanecarboxylate.
$R_f$=0.25 (hexane/AcOEt 95/5).

EXAMPLE 33

1-(5-nitro-2-furyl)2-propynyl [1R-[1α,3α(Z)]]-2,2-dimethyl-3-(3,3,3-trifluoro-2-chloropropenyl)cyclopropanecarboxylate.
$R_f$=0.35 (hexane/AcOEt 7/3).

EXAMPLE 34

(5-propynyl-2-furyl)methyl[1R-[1α,3α(Z)]]-2,2-dimethyl-3-(3,3,3-trifluoro-2-chloropropenyl)cyclopropanecarboxylate.

EXAMPLE 35

(5-propynyl-2-furyl)methyl [1R-[1α,3α(Z)]]-2,2-dimethyl-3-(2-fluoro-3-methoxy-3-oxo-1-propenyl)cyclopropanecarboxylate.
$R_f$=0.2 (hexane/AcOEt 9/1).

EXAMPLE 36

(5-hydroxymethyl-2-furyl)methyl [1R- [1α,3α(Z)]]-2,2-dimethyl-3-(2-fluoro-3-methoxy-3-oxo-1-propenyl)cyclopropanecarboxylate.
$R_f$=0.3 (hexane/AcOEt 5/5).

EXAMPLE 37

(5-trifluoromethyl-2-furyl)methyl[1R-[1α,3α(Z)]]-2,2-dimethyl-3-(3,3,3-trifluoro-2-chloropropenyl)cyclopropanecarboxylate.
$R_f$=0.2 (hexane/isopropyl ether 95/5).

EXAMPLE 38

(5-cyano-2-furyl)methyl[1R-[1α,3α(Z)]]-2,2-dimethyl-3-(3,3,3-trifluoro-2-chloropropenyl)cyclopropanecarboxylate.
$R_f$=0.27 (hexane/AcOEt 8/2).

EXAMPLE 39

1-(3-thienyl)-2-propynyl[1R-[1α,3α(Z)]]-2,2-dimethyl-3-(3,3,3-trifluoro-2-chloropropenyl)cyclopropanecarboxylate.
$R_f$=0.2 (hexane/AcOEt 95/5).

EXAMPLE 40

1-(3-thienyl)-2-propynyl [1R-[1α,3α(Z)]]-2,2-dimethyl-3-(2-fluoro-3-methoxy-3-oxo-1-propenyl)cyclopropanecarboxylate.
$R_f$=0.35 (hexane/AcOEt 8/2).

EXAMPLE 41

1-(2-thienyl)-2-propynyl[1R-[1α,3α; (Z)]]-2,2-dimethyl-3-(3,3,3-trifluoro-2-chloropropenyl)cyclopropanecarboxylate.
$R_f$=0.25 (hexane/AcOEt 95/5).

EXAMPLE 42

1-(2-thienyl)-2-propynyl [1R-[1α,3α(Z)]]-2,2-dimethyl-3-(2-fluoro-3-methoxy-3-oxo-1-propenyl)cyclopropanecarboxylate.
$R_f$=0.25 (hexane/AcOEt 8/2).

EXAMPLE 43

(5-difluoromethyl-2-thienyl)methyl[1R-[1α,3α(Z)]]-2,2-dimethyl-3-(3,3,3-trifluoro-2-chloropropenyl)cyclopropanecarboxylate.

$R_f$=0.2 (hexane/isopropyl ether 95/5).

EXAMPLE 44

1-(5-difluoromethyl-2-thienyl)-2-propynyl[1R-[1α,3α(Z)]]-2,2-dimethyl-3-(3,3,3-trifluoro-2-chloropropenyl)cyclopropanecarboxylate.

$R_f$=0.4 (hexane/AcOEt 8/2).

EXAMPLE 45

1-(5-difluoromethyl-2-thienyl)-2-propynyl [1R-[1α,3β(Z)]]-2,2-dimethyl-3-(2-fluoro-3-methoxy-3-oxo-1-propenyl)cyclopropanecarboxylate.

$R_f$=0.23 (hexane/AcOEt 8/2).

EXAMPLE 46

1-(3-chloro-5-difluoromethyl-2-thienyl)-2-propynyl [1R-[1α,3α(Z)]]-2,2-dimethyl-3-(3,3,3-trifluoro-2-chloropropenyl)cyclopropanecarboxylate.

$R_f$=0.12 (hexane/AcOEt 95/5).

Preparation 3

(4-trifluoromethyl-2-furyl)-2-propynol.

Stage A: Ethyl 2-methyl-4-hydroxy-4-trifluoromethyl-4,5-dihydrofuran-3-carboxylate.

A solution of 18.8 g of sodium hydride in 175 ml of ethanol was added over 3 hours into a mixture of 51 g of ethyl acetoacetate, 74.8 g of 1-bromo-3,3,3-trifluoroacetone and 200 ml of toluene while maintaining a temperature below +10° C. The mixture was stirred for 18 hours and an aqueous sodium bicarbonate solution was added. The mixture was stirred and extracted with isopropyl ether. The extract was dried and the solvent was evaporated to obtain 62 g of the expected product with a boiling point of 64°–72° C.

Stage B: Ethyl 2-methyl-4-trifluoromethyl-3-furancarboxylate.

10 g of the product of Stage A were heated for 7 hours at reflux in 50 ml of toluene in the presence of 0.5 g of toluenesulfonic acid and the mixture was allowed to return to room temperature. The solvent was evaporated and the residue was chromatographed on silica (eluent: 95/5 n-hexane/ethyl acetate) to obtain 6.95 g of the expected product.

Stage C: 2-methyl-4-trifluoromethyl-3-furancarboxylic acid.

18 g of the product of Stage B were refluxed for 2 and a half hours in 42 ml of water and 126 ml of ethanol in the presence of 3.55 g of sodium hydroxide. The mixture was allowed to return to room temperature and 2N hydrochloric acid was added to neutrality. The mixture was partially concentrated and 2N sodium hydroxide solution was added. The mixture was extracted with isopropyl ether and the solvent was evaporated to obtain 14.25 g of the expected product melting at 140° C.

Stage D: 2-methyl-4-trifluoromethylfuran.

13.45 g of the product obtained in Stage C were heated at 240° C. for 30 minutes in the presence of 0.6 g of copper (II) sulfate and 10 ml of quinoline. The reaction mixture was dried and distilled under atmospheric pressure to obtain 6.2 g of the expected product with a boiling point of 72°–74° C.

Stage E: 2-bromomethyl-4-trifluoromethylfuran.

6 g of the product of Stage D were refluxed for 1 and a half hours in 50 ml of carbon tetrachloride in the presence of 7.2 g of N-bromosuccinimide and 0.3 g of azobisisobutyronitrile and the mixture was allowed to return to room temperature and was filtered. The solvent was evaporated and the residue was chromatographed on silica (eluent: 98/2 ether/isopropyl ether) to obtain 5.5 g of the expected product.

Stage F: 4-trifluoromethyl-2-furancarboxaldehyde.

2.95 g of the product of Stage E, 9 ml of water and 3.6 g of hexamethylenetetramine were refluxed for 1 hour. 9 ml of concentrated hydrochloric acid were added. Reflux was maintained for an additional 1 hour and the mixture was allowed to return to room temperature, diluted with water and extracted with methylene chloride. The extract was washed with water and dried and the solvent was evaporated to obtain 1.9 g of the expected product.

Stage G: 1-(4-trifluoromethyl-2-furyl)-2-propynol.

1.8 g of the product of Stage F were cooled to 0°/+5° C. in 20 ml of tetrahydrofuran and 24 ml of ethynylmagnesium bromide were added over 30 minutes. The mixture was allowed to return to room temperature and was then poured into a saturated aqueous sodium bicarbonate solution and extracted with methylene chloride. The extract was dried and the solvent was evaporated to obtain 0.8 g of the expected product after chromatography on silica (eluent: methylene chloride).

Preparation 4

2-trifluoromethyl-3-furanmethanol.

Stage A: ethyl 2-hydroxy-2-trifluoromethyl-2,5-dihydrofuran-3-carboxylate and ethyl 4-hydroxy-2-trifluoromethyl-4,5-dihydrofuran-3-carboxylate (mixture).

210 ml of chloroacetaldehyde were added over 30 minutes at 20° C. to 36.5 ml of ethyl 4,4,4-trifluoroacetoacetate in 600 ml of pyridine and the mixture was stirred for 52 hours. The reaction mixture was poured into 650 ml of concentrated hydrochloric acid and ice, stirred for 5 minutes and extracted with isopropyl ether. The extract was dried and the solvent was evaporated to obtain after chromatography on silica (eluent: 7/3 hexane/ethyl acetate), 43 g of the expected product.

Stage B: ethyl 2-trifluoromethyl-3-furancarboxylate.

43.g of the product of Stage A were refluxed for 2 and a half hours in 250 ml of toluene and 3.1 g of toluenesulfonic acid and the reaction mixture was allowed to cool and was chromatographed on silica (eluent: 9/1 hexane/ethyl acetate) to obtain after evaporation of the solvent at 40° C. under 80 mm of Hg, 20 g of the expected product.

Stage C: 2-trifluoromethyl-3-furanmethanol.

20 g of the product of Stage B were cooled to −60° C. in 200 ml of toluene, 160 ml of diisobutylaluminium hydride were added dropwise. The mixture was stirred for 1 and a half hours at −60° C. and was then poured into sodium potassium double tartrate and extracted with methylene chloride. The solvent was evaporated and the residue was chromatographed on silica (eluent: 7/3 hexane/ethyl acetate) to obtain 16 g of the expected product.

Preparation 5

2-trifluoromethyl-5-(2-propynyl)-3-furanmethanol.

Stage A: ethyl 4-oxo-2-(2,2,2-trifluoro-1-oxoethyl)-pentanoate.

36.8 g of ethyl 4,4,4-trifluoroacetoacetate were mixed in 400 ml of tetrahydrofuran and 9.6 g of sodium hydride were added at 15° C. over 30 minutes. The mixture was stirred at 20° C. for 1 hour and 0.4 g of potassium iodide and 100 ml of acetone were added. 21 g of chloroacetone in 75 ml of tetrahydrofuran were added dropwise over 15 minutes and the mixture was refluxed for 96 hours and then distilled to obtain 24.4 g of the expected product with a boiling point of 65° C. (0.2 mbar).

Stage B: ethyl 2-trifluoromethyl-5-methyl-3-furancarboxylate.

24 g of the product of Stage A were mixed in 150 ml of toluene and 1.85 g of toluenesulfonic acid were added. The mixture was refluxed for 20 hours. The solvent was evaporated under reduced pressure at 40° C. The residue was chromatographed on silica (eluent: 95/5 hexane/ethyl acetate) to obtain 13.5 g of the expected product.

Stage C: ethyl 2-trifluoromethyl-5-bromomethyl-3-furancarboxylate.

Using the procedure of Preparation 3, Stage E, 12.4 g of the product of Stage B were reacted to obtain 12.8 g of the expected product.

Stage D: 2-trifluoromethyl-5-bromomethyl-3-furanmethanol.

Using the procedure of Preparation 4, Stage C, 4.65 g of the product of Stage C were reacted to obtain 4 g of the expected alcohol.

Stage E: 2-trifluoromethyl-5-bromomethyl-3-(tetrahydropyranyloxymethyl)furan.

2.82 ml of dihydropyran and 250 mg of toluenesulfonic acid were added to 4 g of the product of Stage D in 80 ml of ether and the mixture was stirred for 3 hours at 20° C. The solvent was evaporated under reduced pressure and the residue was chromatographed on silica (eluent: 9/1 hexane/ethyl acetate) to obtain 4.8 g of the expected product.

Stage F: 2-trifluoromethyl-5-(2-propynyl)-3-(tetrahydropyranyloxymethyl)furan.

90 ml of ethynyl magnesium bromide as a 1M solution in tetrahydrofuran and 1.8 g of copper chloride were added to 6.18 g of the product of Stage E in 15 ml of tetrahydrofuran and the mixture was refluxed for 18 hours, cooled to 20° C., poured into a saturated aqueous sodium dihydrogenphosphate solution, and extracted with isopropyl ether. The extract was dried and the solvent evaporated. The residue was chromatographed on silica (eluent: 9/1 hexane/isopropyl ether) to obtain 1.5 g of the expected product.

Stage G: 2-trifluoromethyl-5-(2-propynyl)-3-furanmethanol.

1.1 g of the product of Stage F were mixed in 25 ml of methanol and 50 mg of toluenesulfonic acid were added. The mixture was stirred at 20° C. for 2 hours and poured into ice-cold water and extracted with isopropyl ether. The extract was dried and the solvent was evaporated. The residue was chromatographed on silica (eluent: 7/3 hexane/ethyl acetate) to obtain 600 mg of the expected alcohol.

Preparation 6

1-(5-trifluoromethyl-2-furyl)-2-propynol.

Stage A: 2-trifluoromethyl-5-methyl-3-furancarboxylic acid.

13 g of the product of Stage B of Preparation 5, 100 ml of methanol and 38.5 ml of 2N sodium hydroxide solution were refluxed for 1 hour and the solvent was evaporated. The residue was taken up in water, washed with 50 ml of isopropyl ether and acidified with 6.5 ml of hydrochloric acid. The crystals were filtered off, washed with water and dried at 20° C. under reduced pressure to obtain 10.33 g of the expected product.

Stage B: 5-trifluoromethyl-2-methylfuran.

Using the procedure of Stage D of Preparation 3, 5.3 g of the acid of Stage A were reacted to obtain 3.41 g of the expected product.

Stage C: 5-trifluoromethyl-2-(bromomethyl)furan.

Using the procedure of Stage E of Preparation 3, 3.41 g of the product of Stage B were reacted to obtain after chromatography on silica (eluent: 95/5 hexane/isopropyl ether), 3.5 g of the expected product.

Stage D: 5-trifluoromethyl-2-furancarboxaldehyde.

5.9 g of N-methylmorpholine N-oxide in 25 ml of methylene chloride and 12.5 ml of dimethyl sulfoxide were added over 15 minutes to 2.5 g of the product of Stage D in 25 ml of methylene chloride. The mixture was stirred at 20° C. for 5 hours, poured into an aqueous sodium dihydrogenphosphate solution, and extracted with methylene chloride. The extract at 30° C. (620 mbar). After chromatography on silica (eluent: methylene chloride), the crude product obtained was used as is in the following stage.

Stage E: 1-(5-trifluoromethyl-2-furyl)-2-propynol.

The mixture of approximately 1.78 g of the product of Stage D and approximately 20 ml of methylene chloride was cooled to +5° C. and 27 ml of ethynylmagnesium bromide as a 0.5M solution in tetrahydrofuran were added over 15 minutes. The mixture was stirred for 15 minutes at +5° C., poured into an aqueous sodium dihydrogenphosphate solution and extracted with methylene chloride. The extract was dried, the solvent was evaporated at 30° C. and the residue was chromatographed on silica (eluent: methylene chloride) to obtain 0.87 g of the expected product.

Preparation 7

1-(2-furyl)-2-propynol.

2 g of 2-furaldehyde in 30 ml of tetrahydrofuran were cooled to 0° C. and 50 ml of a 0.5M solution of ethynyl magnesium bromide in tetrahydrofuran were added dropwise over 15minutes. The mixture was stirred for 1 hour at 0° C., poured into a saturated aqueous sodium dihydrogenphosphate solution and extracted with isopropyl ether. The extract was dried and the solvent was evaporated to obtain 2.5 g of the expected product after chromatography on silica (eluent: 75/25 hexane/ethyl acetate).

Preparation 8

5-methoxymethyl-2-furanmethanol.

6.4 g of 2,5-furandimethanol were dissolved at 20° C. in 120 ml of tetrahydrofuran and 2.4 g of sodium hydride were added over 30 minutes. The mixture was stirred for 2 hours and 60 ml of dimethylformamide and 4.7 ml of dimethyl sulfate were added. The mixture was stirred for 16 hours at 20° C., poured into ice-cold water and acidified with hydrochloric acid. The mixture was extracted with isopropyl ether and the extract was washed with water and dried. The solvent was evaporated and the residue was chromatographed on silica (eluent: 5/5 hexane/ethyl acetate) to obtain 2.97 g of the expected product.

Preparation 9

1-(5-methoxymethyl-2-furyl)-2-propynol.

Stage A: 5-methoxymethyl-2-furancarboxaldehyde.

3 g of the product of Preparation 8 in 30 ml of methylene chloride were added over 15 minutes to a suspension of 5.45 g of pyridinium chlorochromate in 50 ml of methylene chloride. The mixture was stirred for 2 hours at 20° C. and filtered. The solvent was evaporated and the residue was taken up in 10 ml of methylene chloride and chromatographed on silica (eluent: 5/5 ethyl acetate/hexane) to obtain 1 g of the expected product.

Stage B: 1-(5-methoxymethyl-2-furyl)-2-propynol.

Using the procedure of Stage B of Preparation 2, 1 g of the product of Stage A was reacted to obtain 1.16 g of the expected product.

Preparation 10

5-ethynyl-2-furanmethanol.

Stage A: ethyl 5-bromo-2-furancarboxylate.

10 g of 5-bromo-2-furancarboxylic acid were refluxed for 24 hours in 200 ml of ethanol in the presence of 2 ml of thionyl chloride. The solvent was evaporated and the residue was poured into an aqueous sodium bicarbonate solution. The mixture was extracted with ethyl acetate and the extract was dried. The solvent was evaporated to obtain 8.5 g of the expected product.

Stage B: ethyl 5-(trimethylsilylethynyl)-2-furancarboxylate.

A solution of 5 g of the product of Stage A, 15 ml of acetonitrile, 15 ml of triethylamine, 4.5 ml of ethynyltrimethylsilane, 170 mg of (triphenylphosphine)palladium chloride and 30 mg of copper iodide was heated at 40° C. for 2 and a half hours and then allowed to return to room temperature and was poured into an aqueous sodium dihydrogenphosphate solution. The mixture was extracted with ethyl acetate and the extract was washed with water and dried. The solvent was evaporated to obtain after chromatography on silica (eluent: 95/5 hexane/ethyl acetate) 4.75 g of the expected product.

Stage C: 5-ethynyl-2-furanmethanol.

Using the procedure of Preparation 4, Stage C, 4 g of the product of Stage B above were reacted to obtain the expected product.

Preparation 11

1-(5-ethynyl-2-furyl)-2-propynol.

Stage A: 5-ethynyl-2-furancarboxaldehyde.

Using the procedure of Stage A of Preparation 2, 1.7 g of the alcohol of Preparation 10 were reacted to obtain 1.2 g of the expected product.

Stage B: 1-(5-ethynyl-2-furyl)-2-propynol.

Using the procedure of Stage B of Preparation 2, 1.2 g of the aldehyde of Stage A were reacted to obtain 1.05 g of the expected product.

Preparation 12

5-difluoromethyl-3-furanmethanol.

Stage A: ethyl 5-formyl-3-furancarboxylate and ethyl 2-formyl-3-furancarboxylate.

9 ml of phosphorus oxychloride were added at +5° C. to 10 ml of dimethylformamide and the mixture was stirred for 40 minutes and then allowed to return to room temperature. 10 g of ethyl 3-furancarboxylate were added and the mixture was heated for 3 and a half hours at 100°–105° C. and then poured into 300 ml of a sodium carbonate solution and 300 ml of methylene chloride. The solvent was evaporated and the residue was chromatographed on silica (eluent: 8/2 hexane/ethyl acetate) to obtain 6.93 g of the expected product.

Stage B: ethyl 5-difluoromethyl-3-furancarboxylate.

Using the procedure of Stage B of Preparation 1, 10.2 g of aldehyde of Stage A and 10 ml of DAST were reacted to obtain 7.9 g of the expected product and 1.2 g of the corresponding 2-difluoromethyl ester after chromatography on silica (eluent: 9/1 hexane/ethyl acetate).

Stage C: 5-difluoromethyl-3-furanmethanol.

Using the procedure of Stage C of Preparation 4, 7.9 g of the product of Stage B were reacted to obtain 4.8 g of the expected product.

Preparation 13

1-(5-difluoromethyl-3-furyl)-2-propynol.

Stage A: 5-difluoromethyl-3-furancarboxaldehyde.

4.8 g of the alcohol of Preparation 12 in 55 ml of methylene chloride were added to 8.4 g of pyridinium chlorochromate in 90 ml of methylene chloride and the mixture was stirred for 90 minutes and filtered. The solvent was evaporated and the residue was chromatographed on silica eluent: 7/3 hexane/ethyl acetate) to obtain 3.2 g of the expected aldehyde.

Stage B: 1-(5-difluoromethyl-3-furyl)-2-propynol.

Using the procedure of Stage B of Preparation 2, 3.2 g of the aldehyde of Stage A were reacted to obtain 3.8 g of the expected product.

Preparation 14

2-difluoromethyl-3-furanmethanol.

Using the procedure of Stage C of Preparation 4, 1.9 g of the appropriate ester of Preparation 12, Stage B were reacted to obtain 1 g of the expected alcohol.

Preparation 15

1-(5-nitro-2-furyl)-2-propynol.

Using the procedure of Stage B of Preparation 2, 2.82 g of 5-nitro-2-furaldehyde and 45 ml of ethynylmagnesium bromide were reacted to obtain 1.84 g of the expected product after chromatography on silica (eluent: 8/2 hexane/ethyl acetate).

Preparation 16

5-hydroxymethyl-2-furancarbonitrile.

Stage A: 5-formyl-2-furancarbonitrile.

75 ml of tetrahydrofuran and 22.6 ml of diisopropylamine were cooled to −60° C. and 100 ml of 1.6M n-butyllithium in hexane were added over 25 minutes. The mixture was stirred for 1 hour and 13.02 g of 2-furancarbonitrile in 50 ml of tetrahydrofuran were added. The mixture was stirred for 40 minutes at −70° C. and 13 ml of N-dimethylformamide in 25 ml of tetrahydrofuran were added. The mixture was stirred for 2 hours at −70° C. and then poured into an aqueous potassium dihydrogen phosphate solution and extracted with isopropyl ether. The extract was dried and the solvent was evaporated to obtain after chromatography on silica (eluent: 7/3 hexane/ethyl acetate) 3.51 g of the expected product.

Stage B: 5-hydroxymethyl-2-furancarbonitrile.

0.87 g of the aldehyde of Stage A in 5 ml of tetrahydrofuran and 1 ml of water was cooled to 0° C. and 0.47 g of potassium borohydride were introduced. The mixture was stirred for 5 hours, poured into an aqueous sodium dihydrogenphosphate solution and extracted with isopropyl ether. The extract was dried and the solvent was evaporated to obtain 0.77 g of the expected product.

Preparation 17

1-(3-thienyl)-2-propynol.

Using the procedure of Stage B of Preparation 2, 2.5 g of 3-thiophenecarboxaldehyde were reacted to obtain 2.63 g of the expected product.

Preparation 18

1-(2-thienyl)-2-propynol.

Using the procedure of Stage B of Preparation 2, 4 g of 2-thiophenecarboxaldehyde were reacted to obtain 3.92 g of the expected product.

Preparation 19

1-(5-difluoromethyl-2-thienyl)-2-propynol.

Stage A: 2-methyl-5-(difluoromethyl)thiophene.

Using the procedure of Stage B of Preparation 1, 10 ml of 5-methyl-2-thiophenecarboxaldehyde were reacted to obtain 9.45 g of the expected product.

Stage B: 2-bromomethyl-5-(difluoromethyl)thiophene.

Using the procedure of Stage E of Preparation 3, 3.5 g of the product of Stage A were reacted to obtain 3.3 g of the expected product.

Stage C: 5-difluoromethyl-2-thiophenecarboxaldehyde.

Using the procedure of Stage F of Preparation 3, 7.9 g of the product of Stage B were reacted to obtain after chromatography on silica (eluent: 8/2 hexane/ethyl acetate) 3.6 g of the expected product.

Stage D: 1-(5-difluoromethyl-2-thienyl)-2-propynol.

Using the procedure of Preparation 2, Stage B, 3.6 g of the aldehyde of Stage C were reacted to obtain 3 g of the expected product.

Preparation 20

5-difluoromethyl-2-thiophenemethanol.

Using the procedure of Preparation 16, Stage B, the aldehyde of Stage C of Preparation 19 and sodium borohydride in an ethanol/water mixture were reacted to obtain the expected product.

Preparation 21

5-trifluoromethyl-2-furanmethanol.

Using the procedure of Preparation 16, Stage B, the aldehyde of Stage D of Preparation 6 and sodium borohydride in an ethanol/water mixture were reacted to obtain the expected product.

Preparation 22

1-(3-chloro-5-difluoromethyl-2-thienyl)-2-propynol.

Stage A: 4,5-dichloro-2-thiophenecarboxaldehyde.

11.1 g of diisopropylamine in 100 ml of tetrahydrofuran were cooled to −60° C., 49 ml of n-butyllithium were added over 10 minutes. The mixture was stirred for 30 minutes and 10 g of 2,3-dichlorothiophene were added at −60° C. The mixture was stirred for 45 minutes and then 6 ml of dimethylformamide and 10 ml of tetrahydrofuran were added. The mixture was stirred for 1 and a half hours, allowed to return to room temperature, poured into a saturated aqueous sodium dihydrogenphosphate solution and extracted with isopropyl ether. The solvent was evaporated and, after chromatography on silica (eluent: 95/5 hexane/ethyl acetate), 10.16 g of the expected product were obtained.

Stage B: 2,3-dichloro-5-(difluoromethyl)thiophene.

Using the procedure of Stage B of Preparation 1, 7 g of aldehyde of Stage A and 7.6 ml of DAST were reacted to obtain 5.88 g of the expected product.

Stage C: 3-chloro-5-difluoromethyl-2-thiophenecarboxaldehyde.

2.47 g of the product of Stage B were cooled to −60° C. in 20 ml of tetrahydrofuran and 9.2 ml of n-butyllithium were added. The mixture was stirred for 2 hours and 1.4 ml of dimethylformamide and 3 ml of tetrahydrofuran were added. The mixture was stirred for 30 minutes at −60° C., allowed to return to room temperature and the synthesis was continued as shown in Stage A to obtain 0.9 g of the expected product.

Stage D: 1-(3-chloro-5-difluoromethyl-2-thienyl)-2-propynol.

Using the procedure of Stage B of Preparation 2, 0.64 g of the product of Stage C above and 8.5 ml of ethynyl magnesium bromide were reacted to obtain 0.67 g of the expected product.

PREPARATION 23

[1R-[1α,3α(E)]]-2,2-dimethyl-3-[(2,2-difluorocyclopropylidene)methyl]cyclopropanecarboxylic acid and the corresponding E and Z isomers STAGE A: (1,1-dimethyl)ethyl [1R-[1α,3α(R)]]-2,2-dimethyl-3-(1-acetoxypropynyl)cyclopropanecarboxylate.

10.8 ml of acetic anhydride were introduced at 0° C. over 15 minutes into a solution of 8.5 g of (1,1-dimethyl)ethyl [1R-[1α,3α(R)]]-2,2-dimethyl-3-(1-hydroxypropynyl)cyclopropane carboxylate, (European Patent No. 0,105,006) and 25 ml of pyridine. The reaction mixture was stirred 6 hours and then poured into an aqueous sodium dihydrogenphosphate solution and extracted with isopropyl ether. The extract was dried and evaporated to dryness under reduced pressure and the residue was chromatographed on silica by eluting with a hexane/isopropyl ether (7/3) mixture to obtain 9.44 g of product with a $R_f$=0.4. and melting at 67.2° C.

STAGE B: (1,1-dimethyl)ethyl [1R-[1α,3α(R)]]-2,2-dimethyl-3-[1-acetoxy-1-(3,3-difluorocyclopropenyl)methyl]cyclopropanecarboxylate.

A solution of 61.18 g of sodium chlorodifluoroacetate and 230 ml of diglyme was introduced at 160° C. over 2 H 45 into a solution of 10.7 g of the product of Stage A and 50 ml of diglyme. The reaction mixture was stirred for 1 hour, cooled to 20° C. and poured into an aqueous sodium dihydrogenphosphate solution. The mixture was extracted with ether and the extract was dried and evaporated to dryness. The diglyme was removed by taking the product up in pentane and the solution was washed with water, dried and evaporated to dryness. The product was chromatographed on silica by eluting with a hexane/isopropyl ether (85/15) mixture to obtain 8.57 g of the desired product with a $R_f$=0.2.

STAGE C: (1,1-dimethyl)ethyl [1R-[1α,3α(E,Z)]]-2,2-dimethyl-3-[(2,2-difluorocyclopropylidene)methyl]cyclopropane carboxylate, corresponding E isomer and corresponding Z isomer.

26.6 g of triphenylphosphine copper hydride hexamer [φ₃PCuH]₆ were added at room temperature to a solution of 8.57 g of the product of Stage B and 170 ml of toluene and the reaction mixture was stirred for 1 hour. 80 ml of pentane and 80 ml of ethyl ether were added and the mixture was stirred for 2 hours. Clarcel was added and the mixture was stirred again, filtered and evaporated to dryness. The crude product was chromatographed by eluting with a hexane/methylene chloride (95/5) mixture to obtain after evaporating under reduced pressure:
720 mg of E+Z mixture, 2.83 g of Z isomer, $R_f$=0.15 (95/5 hexane/methylene chloride) and 2.97 g of E isomer, $R_f$=0.1, melting at 33.8° C.

STAGE D: [1R-[1α,3α(Z)]]-2,2-dimethyl-3-[(2,2-difluorocyclopropylidene)methyl]cyclopropanecarboxylic acid.

A solution of 2.83 g of the Z isomer of Stage C, 28 ml of toluene and 180 mg of toluenesulfonic acid was refluxed for 1 h 65 minutes and the reaction mixture was cooled to 20° C., poured into ice-cold water and extracted with isopropyl ether. The extract was dried and evaporated to dryness under reduced pressure. The residue was chromatographed by eluting with a hexane/methylene chloride/acetone (70/15/15) mixture and the eluents were evaporated under reduced pressure to obtain 550 mg of the desired product with a $R_f$=0.15 (70/15/15 hexane/methylene chloride/acetone).

[1R-[1α,3α(E)]]-2,2-dimethyl-3-[(2,2-difluorocyclopropylidene)methyl]cyclopropanecarboxylic acid Using the procedure of the preparation of the Z acid, 2.97 g of the starting ester E were reacted to obtain 1.88 g of the desired product with a $R_f$=0.15 (70/15/15 hexane/methylene chloride/acetone) and melting at 78.9° C.

[1R-[1α,3α(E+Z)]]-2,2-dimethyl-3-[(2,2-difluorocyclopropylidene)methyl]cyclopropanecarboxylic acid Using the procedure of the preparation of the Z acid, 720 mg of the E+Z ester were reacted to obtain 320 mg of the desired product with a $R_f$=0.15 (70/15/15 hexane/methylene chloride/acetone).

EXAMPLE 47

Preparation of a soluble concentrate
There is prepared a homogeneous mixture of:
Product of Example 1: 0.25 g
Piperonyl butoxide: 1.00 g
Tween 80: 0.25 g
Topanol A: 0.1 g
Water: 98.4 g

EXAMPLE 48

Preparation of an emulsifiable concentrate
There are intimately mixed:
Product of Example 2: 0.015 g
Piperonyl butoxide: 0.5 g
Topanol A: 0.1 g
Tween 80: 3.5 g
Xylene: 95,885 g

EXAMPLE 49

Preparation of an emulsifiable concentrate
There is prepared a homogeneous mixture of:
Product of Example 1: 1.5 g
Tween 80: 20.00 g
Topanol A: 0.1 g
Xylene: 78.4 g

EXAMPLE 50

Preparation of granules
Granules containing from 0.1% to 5% of active substances were prepared.

BIOLOGICAL STUDY

A—Activity against Diabrotica
The test insects were final-stage larvae of Diabrotica. A filter paper disc with a diameter of 9 cm, arranged at the bottom of a Petri dish was treated with 1 ml of an acetone solution of the product to be tested. After drying, 15 larvae per dose were deposited and mortality was monitored 24 hours after treatment. From a dose of 0.5 ppm, the products of the invention exhibited good activity, especially the products of Examples 1, 5, 7, 9, 10, 12, 18, 19, 26, 27, 28, 30 and 37 and more particularly the product of Example 2.

B—Activity against Blatella
Study of the activity by tarsal contact against the German cockroach.

The tested insects were males of the German cockroach (*Blatella germanica*) and the test was carried out by depositing an acetone solution of specific concentration on the bottom of a Petri dish with a diameter of 20 cm. After drying, 20 male cockroaches per concentration were left to reside for 1 hour, the insects were then transferred into a healthy medium. Their mortality was monitored at 24 hours, 48 hours, 3 and 5 days. The "KD" was thus determined and the result was expressed as a percentage of "KD" cockroaches in 5 minutes, after treatment by the studied product at a dose of 500 mg/l.

The result was 100% for the products of Examples 5, 6, 9, 13, 19, 23, 24, 25, 29, 31, 33, 35, 36, 40, 42 and 45.

Various modifications of the products and method of the invention may be without departing from the spirit or scope thereof and it is to be understood that the invention is intended to be limited only as defined in the appended claims.

What is claimed is:

1. A compound in all possible stereoisomeric forms and mixtures thereof of the formula

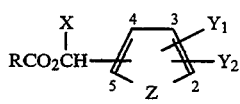   I wherein

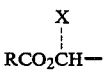

is in position 2 or 3, X is selected from the group consisting of hydrogen, alkyl of 1 to 8 carbon atoms and —C≡N, $Y_1$ and $Y_2$ are individually in position 2, 3, 4 or 5 and one is selected from the group consisting of —NO$_2$, —C≡CH, —CH$_2$—C≡CH, alkyl of 1 to 4 carbon atoms optionally by at least one fluorine and the other is —CHF$_2$ or —CF$_3$, Z is oxygen or sulfur and R is:

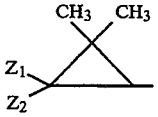

$Z_1$ and $Z_2$ are methyl, or $Z_1$ is hydrogen and either $Z_2$ is:

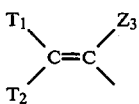

in which $Z_3$ is hydrogen or halogen and $T_1$ and $T_2$ are individually selected from the group consisting of hydrogen, halogen, alkoxy and alkyl of 1 to 8 carbon atoms optionally substituted by at least one member of the group consisting of halogen, mono-, di- or trifluoromethyl, cyano and phenyl optionally substituted by halogen, or $T_1$ and $T_2$ together form a cycloalkyl of 3 to 6 carbon atoms—or $Z_2$ is

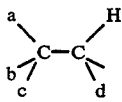

in which a, b, c and d are individually halogen—or $Z_2$ is:

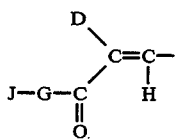

in which D is hydrogen or halogen or alkoxy of 1 to 8 carbon atoms, G is oxygen or sulfur and J is optionally unsaturated alkyl of up to 8 carbon atoms optionally substituted by at least one member of the group consisting of halogen and cyano, or aryl of 6 to 14 carbon atoms optionally substituted by at least one member of the group consisting of halogen and cyano.

2. A compound of claim 1 wherein Z is oxygen.
3. A compound of claim 1 wherein

is in the 2- position.

4. A compound of claim 1 wherein $Y_1$ or $Y_2$ is —CHF$_2$.
5. A compound of claim 1 wherein $Y_1$ or $Y_2$ is —CF$_3$.
6. A compound of claim 1 wherein one of $Y_1$ or $Y_2$ is —NO$_2$, —C≡CH or —CH$_2$—C≡CH.
7. A compound of claim 1 wherein X is hydrogen.
8. A compound of claim 1 wherein X is ethynyl.
9. A compound of claim 1 wherein R is derived from an acid derived from cyclopropanecarboxylic acid in which the cyclopropane copula has the (1R)-cis structure.
10. A compound of claim 1 wherein R is:

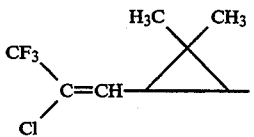

in all its possible stereoisomeric forms, as well as their mixtures.

11. A compound of claim 1 selected from the group consisting of: (5-difluoromethyl-2-furyl)methyl [1R-[1α,3α(Z)]]-2,2-dimethyl-3-(3,3,3-trifluoro-2-chloropropenyl)cyclopropane carboxylate; 1-5-difluoromethyl-2-furyl)2-propynyl [1R-[1α,3α(Z)]]-2,2-dimethyl-3-(2-fluoro-3-methoxy-3-oxo-1-propenyl)cyclopropane carboxylate; 1-(5-difluoromethyl-2-furyl)methyl [1R-[1α,3α(Z)]]-2,2-dimethyl-3-(2,2-dichloroethenyl)cyclopropane carboxylate; 1-(5-difluoromethyl-2-furyl)2-propynyl [1R-[1α,3α(Z)]]-2,2-dimethyl-3-(2,2-difluorocyclopropylidene)methyl cyclopropane carboxylate; 1-(5-difluoromethyl-2-furyl)-2-propynyl [1R-[1α,3α(Z)]]-2,2-dimethyl-3-[3-(1-trifluoromethyl)-(2,2,2-trifluoroethoxy)-3-oxo-1-propenyl]cyclopropane carboxylate; (S)-1-(5-difluoromethyl-2-furyl)-2-propynyl [1R-[1α,3α(Z)]]-2,2-dimethyl-3-(3,3,3-trifluoro-2-chloropropenyl)cyclopropane carboxylate and (R)-1-(5-difluoromethyl-2-furyl)-2-propynyl [1R-[1α,3α(Z)]]-2,2-dimethyl-3-(3,3,3-trifluoro-2-chloropropenyl)cyclopropane carboxylate; 1-(5-trifluoromethyl-2-furyl)-2-propynyl [1R-[1α,3α(Z)]]-2,2-dimethyl-3-(3,3,3-trifluoro-2-chloropropenyl)cyclopropane carboxylate; 1-(5-trifluoromethyl-2-furyl)-2-propynyl [1R-[1α,3α(Z)]]-2,2-dimethyl-3-(2-fluoro-3-methoxy-3-oxo-1-propenyl)cyclopropane carboxylate; (5-ethynyl-2-furyl)methyl [1R-[1α,3α(Z)]]-2,2-dimethyl-3-(3,3,3-trifluoro-2-chloropropenyl)cyclopropane carboxylate; 1-(5-ethynyl-2-furyl)-2-propynyl [1R-[1α,3α(Z)]]-2,2-dimethyl-3-(3,3,3-trifluoro-2-chloropropenyl)cyclopropane carboxylate; (2-difluoromethyl-4-furyl)methyl [1R-[1α,3α(Z)]]-2,2-dimethyl-3-(3,3,3-trifluoro-2-chloropropenyl)cyclopropane carboxylate; 1-(2-difluoromethyl-4-furyl)-2-propynyl [1R-[1α,3α(Z)]]-2,2-dimethyl-3-(3,3,3-trifluoro-2-chloropropenyl)cyclopropane carboxylate; and (5-trifluoromethyl-2-furyl)methyl[1R-[1α,3α(Z)]]-2,2-dimethyl-3-(3,3,3-trifluoro-2-chloropropenyl)cyclopropane carboxylate.

12. A compound of claim 1 which is: (5-difluoromethyl-2-furyl)-2-propynyl [1R-[1α,3α(Z)]]-2,2-dimethyl-3-(3,3,3-trifluoro-2-chloropropenyl)cyclopropane carboxylate.

13. An insecticidal composition comprising an insecticidally effective amount of at least one compound of claim 1 and an inert carrier.

14. A method of combatting insects comprising contacting insects with an insecticidally effective amount of at least one compound of claim 1.

15. The method of claim 14 wherein the active compound is selected from the group consisting of: (5-difluoromethyl-2-furyl)methyl [1R-[1α,3α(Z)]]-2,2-dimethyl-3-(3,3,3-trifluoro-2-chloropropenyl)cyclopropane carboxylate; 1-5-difluoromethyl-2-furyl)2-propynyl [1R-[1α,3α(Z)]]-2,2-dimethyl-3-(2-fluoro-3-methoxy-3-oxo-1-propenyl)cyclopropane carboxylate; 1-(5-difluoromethyl-2-furyl)methyl [1R-[1α,3α(Z)]]-2,2-dimethyl-3-(2,2-dichloroethenyl)cyclopropane carboxylate; 1-(5-difluoromethyl-2-furyl)2-propynyl [1R-[1α,3α(Z)]]-2,2-dimethyl-3-(2,2-difluorocyclopropylidene)methyl cyclopropane carboxylate; 1-(5-difluoromethyl-2-furyl)-2-propynyl [1R-[1α,3α(Z)]]-2,2-dimethyl-3-[3-(1-trifluoromethyl)-(2,2,2-trifluoroethoxy)-3-oxo-1-propenyl]cyclopropane carboxylate; (S)-1-(5-difluoromethyl-2-furyl)-2-propynyl [1R-[1α,3α(Z)]]-2,2-dimethyl-3-(3,3,3-trifluoro-2-chloropropenyl)cyclopropane carboxylate and (R)-1-(5-difluoromethyl-2-furyl)-2-propynyl [1R-[1α,3α(Z)]]-2,2-dimethyl-3-(3,3,3-trifluoro-2-chloropropenyl)cyclopropane carboxylate; 1-(5-trifluoromethyl-2-furyl)-2-propynyl [1R-[1α,3α(Z)]]-2,2-dimethyl-3-(3,3,3-trifluoro-2-chloropropenyl)cyclopropane carboxylate;

1-(5-trifluoromethyl-2-furyl)-2-propynyl [1R-[1α,-3α(Z)]]-2,2-dimethyl-3-(2-fluoro-3-methoxy-3-oxo-1-propenyl)cyclopropane carboxylate; (5-ethynyl-2-furyl)methyl [1R-[1α,3α(Z)]]-2,2-dimethyl-3-(3,3,3-trifluoro-2-chloropropenyl)cyclopropane carboxylate; 1-(5-ethynyl-2-furyl)-2-propynyl [1R-[1α,3α(Z)]]-2,2-dimethyl-3-(3,3,3-trifluoro-2-chloropropenyl)cyclopropane carboxylate; (2-difluoromethyl-4-furyl)methyl [1R-[1α,3α(Z)]]-2,2-dimethyl-3-(3,3,3-trifluoro-2-chloropropenyl)cyclopropane carboxylate; 1-(2-difluoromethyl-4-furyl)-2-propynyl [1R-[1α,3α(Z)]]-2,2-dimethyl-3-(3,3,3-trifluoro-2-chloropropenyl)cyclopropane carboxylate; and (5-trifluoromethyl-2-furyl)methyl[1R-[1α,3α(Z)]]-2,2-dimethyl-3-(3,3,3-trifluoro-2-chloropropenyl)cyclopropane carboxylate.

16. The method of claim 14 wherein the active compound is (5-difluoromethyl-2-furyl)-2-propynyl [1R-(1α,3α,(Z)]]-2,2-dimethyl-3-(3,3,3-trifluoro-2-chloropropenyl)-cyclopropane carboxylate.

* * * * *